US006630152B2

(12) United States Patent
Chou

(10) Patent No.: US 6,630,152 B2
(45) Date of Patent: *Oct. 7, 2003

(54) ALOE VERA GLOVE AND MANUFACTURING METHOD

(75) Inventor: Belle L Chou, Union City, CA (US)

(73) Assignee: Shen Wei (USA), Inc., Union City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/938,715

(22) Filed: Aug. 23, 2001

(65) Prior Publication Data

US 2002/0025335 A1 Feb. 28, 2002

Related U.S. Application Data

(63) Continuation-in-part of application No. 09/898,632, filed on Jul. 3, 2001, now Pat. No. 6,423,328, which is a continuation of application No. 09/288,067, filed on Apr. 7, 1999, now Pat. No. 6,274,154.

(51) Int. Cl.[7] .......................... A01N 25/34; A41D 19/00

(52) U.S. Cl. ............................... 424/402; 2/158; 2/159; 2/161.7; 2/168; 2/169

(58) Field of Search ................................ 424/402, 443; 2/158, 159, 161.7, 168, 169

(56) References Cited

U.S. PATENT DOCUMENTS

| 4,122,554 A | * | 10/1978 | Stager |
| 4,185,330 A | * | 1/1980 | Stager |
| 4,186,445 A | * | 2/1980 | Stager |
| 4,775,372 A | * | 10/1988 | Wilberg |
| 5,417,968 A | * | 5/1995 | Staats |
| 5,614,202 A | * | 3/1997 | DeFina |
| 5,682,617 A | * | 11/1997 | Tumas |
| 5,869,072 A | * | 2/1999 | Berry |
| 5,910,567 A | * | 6/1999 | Tanaka et al. |
| 6,117,119 A | * | 9/2000 | Gould |
| 6,274,154 B1 | | 8/2001 | Chou .................. 424/402 |
| 6,423,328 B2 | | 7/2002 | Chou |
| 2001/0006680 A1 | * | 7/2001 | Mansouri |

FOREIGN PATENT DOCUMENTS

| JP | 409002962 | * | 1/1997 |
| WO | 94/12115 | * | 6/1994 |
| WO | WO 00/15431 | | 3/2000 |
| WO | WO 00/59450 | | 10/2000 |

OTHER PUBLICATIONS

"Le soothe™ Aloe Vera & Vitamin E Latex Glove Examination", 2 page Product Brochure (2002).
"Le soothe™ Aloe Vera & Vitamin E Powder Free Latex Exam Glove", 1 page Product Brochure (2002).
Mayo Health Web page, "Your Body's First Line of Defense," 1 page Jun. 19, 1999.
Mayo Health Web page, "The Anatomy of Your Skin," 1 page Jun. 19, 1999.
IASC Website, "Aloe Vera: Its Potential Use in Wound Healing and Disease Control in Oral Conditions By Dr. Timothy E. Moore, D.D.S./M.S., P.C.," 2 pages May 12, 1999.
Safeskin™ Powder–Free Latex Gloves Product Packaging; Kimberly–Clark Corporation, 2001 (6 pages).

(List continued on next page.)

Primary Examiner—Thurman K. Page
Assistant Examiner—Robert M. Joynes
(74) Attorney, Agent, or Firm—Intellectual Property Law Group LLP; Otto O. Lee; C. George Yu

(57) ABSTRACT

A protective glove includes a coating of dehydrated material on its inside surface. The dehydrated material, in contact with perspiration from a hand wearing the glove, soothes the hand. Some methods of placing the coating onto the inside surface of the glove include spraying or dipping with a solution that includes Aloe Vera.

17 Claims, 4 Drawing Sheets

OTHER PUBLICATIONS

Crosstex® International Aloe Vera Ultra Plus® Powderless Product Packaging for Small Non–Clorinated Powderless Exam Gloves; about Dec., 2001 (6 pages).

Ultra Preserve with Aloe Vera Packaging for Polytex™ Lined Rubber LateX Examination Gloves; Tillotson Healthcare Corporation (undated) (6 pages).

Packaging for AloeDerm® Textured Powder–Free with Aloe Vera; Top Quality Manufacturing Inc. (undated) (6 pages).

Promotional Letter to Dental Professionals from Quantum re: SoftSkin®With Aloe Vera (undated) (2 pages).

Informational brochure re: Softskin® Powder–Free Latex Exam Gloves with Aloe Vera (undated) ( 2 pages).

Promotional advertisement from Quantum Labs Incorporated re: SoftSkin®With Aloe Vera (undated) (1 page).

Packaging for SoftSkin® With Aloe Vera Powder–Free Latex Exam Gloves; Quantum Labs Incorporated (undated) (2 pages).

Sale of Quantum/Softskin® as described in the above softskin® literature labeled C10–C13 (approx. May/1999) (1 page).

Introductory brochure for Aloetouch® distributed by Medline Industries, Inc. 2000 (2 pages).

Sale of Aloetouch® Glove to Medline as described in the above literature labeled C15 (approx. Oct./1999) (1 page).

* cited by examiner

ALOE VERA GLOVE AND MANUFACTURING METHOD

CROSS REFERENCE

This is a continuation-in-part of commonly owned U.S. Pat. application Ser. No. 09/898,632, filed Jul. 3, 2001, now U.S. Pat. No. 6,425,328 which is a continuation of U.S. Pat. application Ser. No. 09/288,067, now U.S. Pat. No. 6,274,154, filed Apr. 7, 1999. These prior patent application(s) are hereby incorporated by reference in their entirety for all purposes.

BACKGROUND

Disposable gloves, for example, disposable examination gloves, are widely used as a protective measure to insulate hands from the objects handled by the wearer of gloves. To allow ease in handling objects, disposable gloves are made of thin and elastic material to minimize the space between the skin and the glove. Due to poor air circulation resulting from tight insulation, hand sweating is a common problem among glove wearers. Prolonged wearing of disposable gloves causes a moist environment on the surface of the hand that allows viruses, bacteria, yeast and fungus to grow and multiply. Itchiness is a frequent result of wearing disposable examination gloves for extended periods.

Powders are commonly used on the inner surface of gloves to alleviate sweating and to make donning, wearing and removal of gloves easier. However, continuous sweating can easily overwhelm the thin layer of powder that is commonly attached to the surface of the glove. This is especially the case when continuous and frequent wearing of gloves is required. For example, dentists may continuously wear gloves during a dental surgical procedure for up to 40 minutes. In addition, hand washing is necessary after the use of powdered gloves. Frequent hand washing to remove powders may also cause excess dryness of the skin.

The need for disposable gloves that can prevent adverse side effects caused by extensive use is apparent. Various patents disclose different types of gloves that contain lotions. During glove use the lotions come into contact human skin and condition the skins. For example, U.S. Pat. No. 5,614,202 discloses a moisturizing glove that contains a middle layer saturated with lotion. The porous inner layer allows the lotion to pass through and contact the skin. U.S. Pat. Nos. 4,186,445 and 4,185,330 disclose gloves that have inner lining made of a lotion absorbent material. By impregnating the lotion onto the absorbent material, the lotion can condition the hands during application of the gloves.

A common feature of the above disclosures is the use of multiple layers in the glove design. Compared to single layer disposable gloves, the complex design of multiple layer gloves makes production far more costly. Most importantly, the thickness of the layers and the complicated structures of the gloves hinder hand flexibility when the glove wearer tries to pick up and manipulate objects. Such multiple layer designs are suitable for moisturizing hands, but are not suitable for manipulating objects, especially for professions that require handling of fine tasks with precision.

Disposable gloves are generally made of three types of materials: natural rubber latex, acrylonitrile, and polyvinyl chloride.

Natural rubber latex is sensitive to oil-based substances. Prolonged contact between latex and oil-based substance can adversely affect durability and flexibility of the latex material. Most commercially available lotions contain oil-based substances. The use of lotions in prior arts will substantially shorten the shelf life of a natural rubber glove.

There is therefore a need for low cost disposable gloves that can apply moisturizing and therapeutic substances to the hands during the glove use without leaving a greasy feel or look to the skin, while at the same time, retain the characteristics and functions of conventional single layer gloves.

SUMMARY

Some embodiments of the present invention satisfy these needs. Some embodiments of the present invention include a novel disposable glove with Aloe Vera uniformly applied to the inner surface of the glove through a dehydration process, and a method for making such a glove.

One object of some embodiments of the present invention is to condition and soothe the hands during glove use.

Another object of some embodiments of the present invention is to produce a glove that is equivalent to a single layer glove in the user's ability to pick up and manipulate objects.

Still another object of some embodiments of the present invention is to prevent growth of bacteria, viruses, yeast and fungi on the hands, which become more active in a wet environment resulting from sweating during prolonged or frequent wearing of gloves.

A related object is to cause the anti-microbial substance to dissociate and release from the glove surface in response to the degree of wetness of hand.

A further object is to preserve the shelf life of glove by using natural non-oil based substance and to preserve the activity of the therapeutic substance by keeping the substance in a dehydrated state.

The above objects are accomplished, for example, by applying Aloe Vera evenly to the inner surface of a disposable examination glove through dehydration.

The objects are further accomplished, for example, by a method of manufacturing the Aloe Vera glove. The disposable gloves are first treated with chlorine solution to wash off any powders, extract soluble substances in the composite material, and kill microorganisms. After drying, the gloves are turned inside out and dipped into a prepared Aloe Vera solution to saturate the outer surface. The gloves are then dried in a tumbling heater within a controlled narrow range of temperature between 45° C. and 65° C., and for a specific length of time. This causes water to evaporate and the Aloe Vera to evenly coat the glove surface. After cooling to room temperature, the gloves are inverted so that the side with Aloe Vera coating is facing inside.

One embodiment of the present invention is a method of manufacturing protective gloves. The method comprises forming a glove on a mold; applying a solution that includes Aloe Vera onto the glove while the glove is on the mold; at least partially drying the solution that has been applied onto the glove while the glove is on the mold; and removing the glove from the mold.

Another embodiment of the present invention is a method of manufacturing protective gloves. The method includes applying a solution that includes Aloe Vera onto a plurality of gloves; at least after beginning of the applying step, tumbling the plurality of gloves to expose more surface areas of the gloves to application of the solution; and dehydrating solution that has been applied to the plurality of gloves; wherein the plurality of gloves become coated with a dried coating that includes Aloe Vera.

DETAILED DESCRIPTION OF EMBODIMENTS OF THE INVENTION

The following discussion describes in detail one embodiment of the present invention and several variations of, and/or alternatives to, that embodiment. This discussion should not be construed, however, as limiting the present invention to those particular embodiments. Practitioners skilled in the art will recognize numerous other embodiments as well.

Figure 1:
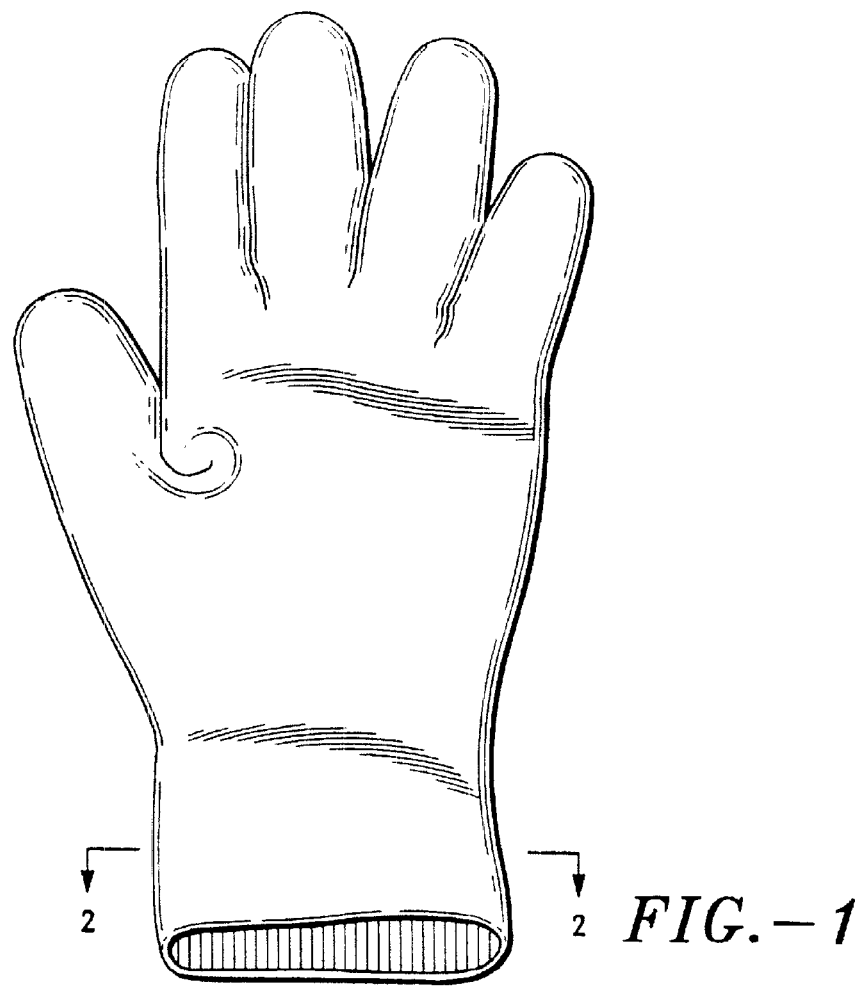
FIG. 1 is the front perspective view of an Aloe Vera glove constructed in accordance with the principles of the present invention.
Figure 2:
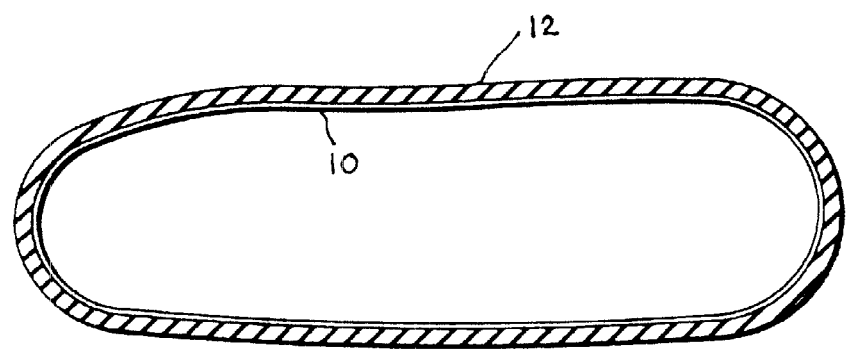
FIG. 2 is a sectional view taken along the lines 2—2 of figure

An embodiment of the present invention is a disposable glove as illustrated in FIG. 1, which has Aloe Vera 10 evenly coated on the inner surface in a dehydrated state, as illustrated in FIG. 2. The glove retains the features of a disposable examination glove, which is simple and convenient to use and allows the wearer to handle fine tasks with precision. Another embodiment of The present invention is a manufacturing method for modifying a disposable glove by coating Aloe Vera on the inner surface of the glove. The glove is coated with Aloe Vera 10 through dehydration that is accomplished by a well-controlled heating process.

A disposable glove is made of various materials to form a layer 12. Resinous materials such as vinyl or polymer materials such as acrylonitrile are common choices. Three commonly used materials for making disposable gloves are natural rubber latex, acrylonitrile and polyvinyl chloride.

In one preferred embodiment, the glove is made of natural rubber latex. Since natural rubber latex is sensitive to oil-based substances, gloves made of natural rubber latex should not be exposed to oil-based substances. In this embodiment, Aloe Vera is used to coat the gloves and it does not contain any detectable oil-based substances. Coating gloves with Aloe Vera does not affect the glove's shelf life. In another preferred embodiment the glove is made of acrylonitrile polymer.

Aloe Vera is a natural plant extract that has a long history of folk medicine usage. Aloe Vera has been used for external treatment of wounds, burns and skin irritations, and internal treatment of various conditions. Aloe Vera is a popular ingredient in skin-care products. It is also a powerful anti-inflammatory and anti-microbial agent. Aloe Vera is soluble in water and contains non-detectable oil content.

Aloe Vera glove retains the characteristic of a disposable glove without any visible modification, and is easy and convenient to use. The affiliation between Aloe Vera and the glove surface is through a force provided by dehydration. Such affiliation is loosened when sweat dissolves Aloe Vera. The longer a glove is worn, the more likely the hand will sweat, and consequently more Aloe Vera will be dissolved and disassociated from the glove surface, and be applied to hand. The active ingredients in Aloe Vera can then condition hand skin and prevent microorganisms from growing under the wet condition.

In one preferred embodiment, 100% Aloe Vera gel is used to coat the gloves. Aloe Vera is evenly and uniformly distributed on the inner surface of the glove at a thickness of about 0.01 millimeter. The association between Aloe Vera and the surface is achieved by a noncovalent force provided through dehydration.

The method of manufacturing gloves involves treating a commercially available disposable glove to eliminate residue powders, soluble substances, and microorganisms, turning the glove inside out, dipping it into an Aloe Vera solution and heating the glove to cause water to evaporate.

A glove is preferably first treated with a chlorine solution or chlorine gas. Chlorine solution can help to sterilize the gloves, to wash off powders, and most importantly for natural latex gloves, to dissolve residual proteins that could potentially trigger severe allergic reactions among repeat users. After the outside surface of the glove is treated with the chlorine solution, it is turned inside out, and the glove is again treated with the chlorine solution. The residue chlorine is neutralized by using ammonia and the gloves are then dried.

An Aloe Vera solution will then be prepared. One hundred percent concentrated Aloe Vera gel is dissolved in distilled water to generate an Aloe Vera solution. The preferred concentration of the solution is about 20%. To associate Aloe Vera with the surface of the glove, Aloe Vera solution can be sprayed onto the surface of the glove. Alternatively, the glove can be immersed into the Aloe Vera solution. The latter method is preferred because it creates a complete and even distribution of the Aloe Vera solution.

In one preferred embodiment, the dipping process is accomplished by grouping a number of gloves in a batch to achieve higher manufacturing efficiency. The gloves are immersed in the solution for at least 10 minutes to allow adequate absorbency.

Aloe Vera is attached to the surface of the glove through a controlled dehydration process. The water in the Aloe Vera solution is caused to evaporate through heating. Although a higher temperature will cause water to evaporate quicker, excess heat may damage the gloves. For example, gloves exposed to excessive heat of over 70° C. may turn brownish and become brittle. To shorten the heat exposure time, a heating oven is preheated to about 45° C. before the gloves are introduced. The oven has a temperature control mechanism to maintain a maximum temperature. In a preferred embodiment the maximum temperature is set at approximately 65° C. and the heating process lasts from about 35 to 40 minutes. The dehydration process provides an affiliation force so that Aloe Vera can remain associated with the glove surface for an extensive period of time.

Even distribution of Aloe Vera on the glove surface maximizes therapeutic treatment of the hand and minimizes contact between the skin and the glove's composite material. Stationary drying is not preferred because the Aloe Vera solution tends to flow in the direction of the force of gravity. In a preferred embodiment the heating oven has a device to tumble during the heating to make Aloe Vera distribute evenly on the glove surface and to form a uniform coating.

Afterward the gloves are cooled to room temperature. The gloves are then inverted so that the surface with the Aloe Vera faces inside.

Figure 3:
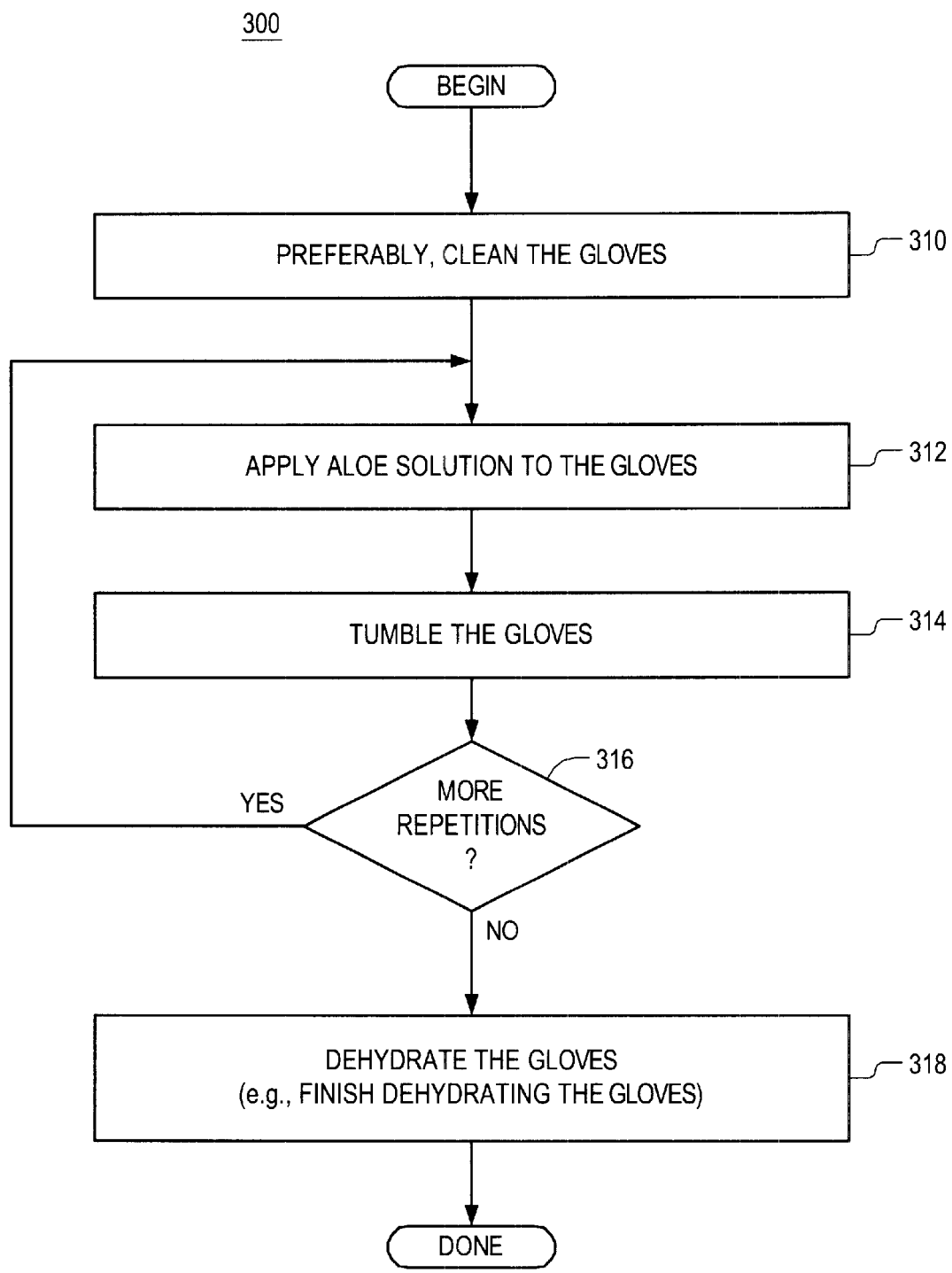
FIG. 3 is a flow diagram that illustrates a method for manufacturing Aloe Vera gloves, preferably using spraying, according to an embodiment of the present invention.

FIG. 3 is a flow diagram that illustrates a method 300 for manufacturing Aloe Vera gloves, preferably using spraying, according to an embodiment of the present invention. The application of Aloe Vera to gloves preferably begins with gloves that are clean and free of protein residue, powder, or other surface contaminants. Therefore, the method 300 preferably begins with a step 310 of cleaning the gloves to remove such contaminants. Next, Aloe Vera solution is applied to the gloves (step 312), preferably by spraying a batch of clean loose gloves that are arranged inside out. The gloves are tumbled (step 314) so that more gloves become better exposed to current or future applying of Aloe Vera solution. Preferably, the tumbling of the gloves in the step 314 occurs, or continues to occur, after the spraying of the Aloe Vera solution in the step 312 has already stopped. The steps 312 and 314 are then preferably repeated for a desired number of iterations (as shown by decision box 316 in FIG. 3). After the last iteration of the step 312 of applying the Aloe Vera solution, the gloves are dried (step 318, or the step 318 and the last iteration of the step 314).

The optional (but preferred) step 310 of cleaning the gloves of surface contaminants can be performed using any competent technique (including any conventional technique). For example, as discussed above, a chlorine solution may be used, and the chlorine solution itself is preferably neutralized and cleaned away at the end of the cleaning step. Cleaning items such as gloves of surface contaminants, for example, using chlorine solution, is a known technology, and the specifics of such cleaning would be readily apparent, depending on the particular type of cleaning equipment being used. For example, for a sufficiently large commercial chlorine washer, a batch of about 3000 to 4000 gloves may be washed using any conventional cycle, for example, a cycle of about 20 to 30 minutes, say, about 23 minutes. Optionally, for extra assurance of cleanliness, the batch of gloves may be further rinsed with water, preferably in a separate commercial washing tank, for example first with hot water and then with cold (e.g., room-temperature) water for any desired amount of time, for example, about 20 to 30 minutes or more. For the method 300, the water is preferably drained well from the gloves. For example, the gloves may be spun dry in the commercial washing tank in conventional manner.

Preferably, the steps 312, 314, and 318 are all performed within a commercial heat tumble dryer, for example, as follows. After the optional water bath at the end of the optional cleaning step 310, the gloves are removed from the water bath and dumped into the heat tumble dryer. The dryer then starts tumbling the gloves. Preferably, the tumbling is accompanied by heating of the gloves by hot air and continues until the gloves are dry or mostly dry. Then, a spray nozzle configured to spray Aloe Vera solution as a fine mist starts spraying the Aloe Vera solution onto the gloves in the dryer. During the spraying, the tumbling may either continue or may continue at a slower pace or may be stopped, and heating of the air may be continued or reduced or stopped. Depending on the level of integration between the spray nozzle and the dryer, the door of the dryer may be opened to allow access to the spray nozzle during spraying. After a period of spraying, the spraying stops and the tumbling continues, or resumes, preferably accompanied by resumed, or continued, heating of the air. The spraying and tumbling are repeated for several iterations. After the last iteration of spraying, the gloves are dried, preferably by tumbling with heating until the gloves are dry. The number and durations of iterations and the amount of solution to use should be chosen to be sufficient, given the particular dryer and spray nozzle configuration, to leave at least a desired minimum thickness, and/or no more than a desired maximum thickness, of dehydrated Aloe Vera on substantially every glove.

For example, for a batch of about 3000 gloves, two kilograms of 20% Aloe Vera solution may be sprayed in about 4 or 5 spray iterations, with the spray iterations spaced about 2 to 5 minutes apart, and with each spray iteration's having a spray duration of about 30 to 90 seconds in a dryer that is the oven discussed above (i.e., one that is limited to a maximum temperature of about 65° C. (preferred) or less than about 80° C.). As shown in FIG. 3, each spray iteration is preferably followed by a tumbling iteration. The final iteration of tumbling is of sufficient duration to dry the gloves and especially should include heating. For example, the final iteration of tumbling may be chosen so that the total duration of tumbling and heating gloves having Aloe Vera solution over all the steps is about 35 to 40 minutes.

Preferably, the method 300 is performed and completed using only two or only three holding containers in which washing, spraying, or tumbling are actually performed. If two containers are used, they would be the chlorine washer and the heat tumble dryer. If three containers are used, they would be the chlorine washer, the water washer, and the heat tumble dryer.

FIG. 3 can also serve as a flow diagram for the earlier-discussed embodiment of the present invention that is a method that uses immersion (e.g., dipping) to apply Aloe Vera solution. If FIG. 3 is interpreted to describe the method that uses immersion, then preferably the decision box 316 reflects having only a single iteration of immersing (the step 312), and the box for step 314 can be interpreted to refer to agitation of the immersion tank, for example, in the manner of a washing machine. After the immersion (e.g., the Steps 312 and 314), the step 318 refers to tumble drying, as has been discussed earlier. If FIG. 3 is used to describe the immersion method, then preferably an extra holding container would be used, namely, an immersion tank that contains the Aloe Vera solution. Thus, if the method 300 is embodied so as to use immersion, then the method 300 is preferably performed and completed using only three or only four holding containers in which washing, immersion, or tumbling are actually performed. If three containers are used, they would be the chlorine washer, the immersion tank for Aloe Vera solution, and the heat tumble dryer. If four containers are used, they would be the chlorine washer, the washer for water, the immersion tank for Aloe Vera solution, and the heat tumble dryer.

In another embodiment of the present invention, a method for manufacturing Aloe Vera gloves is integrated with, and/or includes, the manufacturing of the underlying Aloe Vera-free gloves themselves. This other embodiment is especially preferred for produce large quantities of Aloe Vera gloves efficiently.

Figure 4:
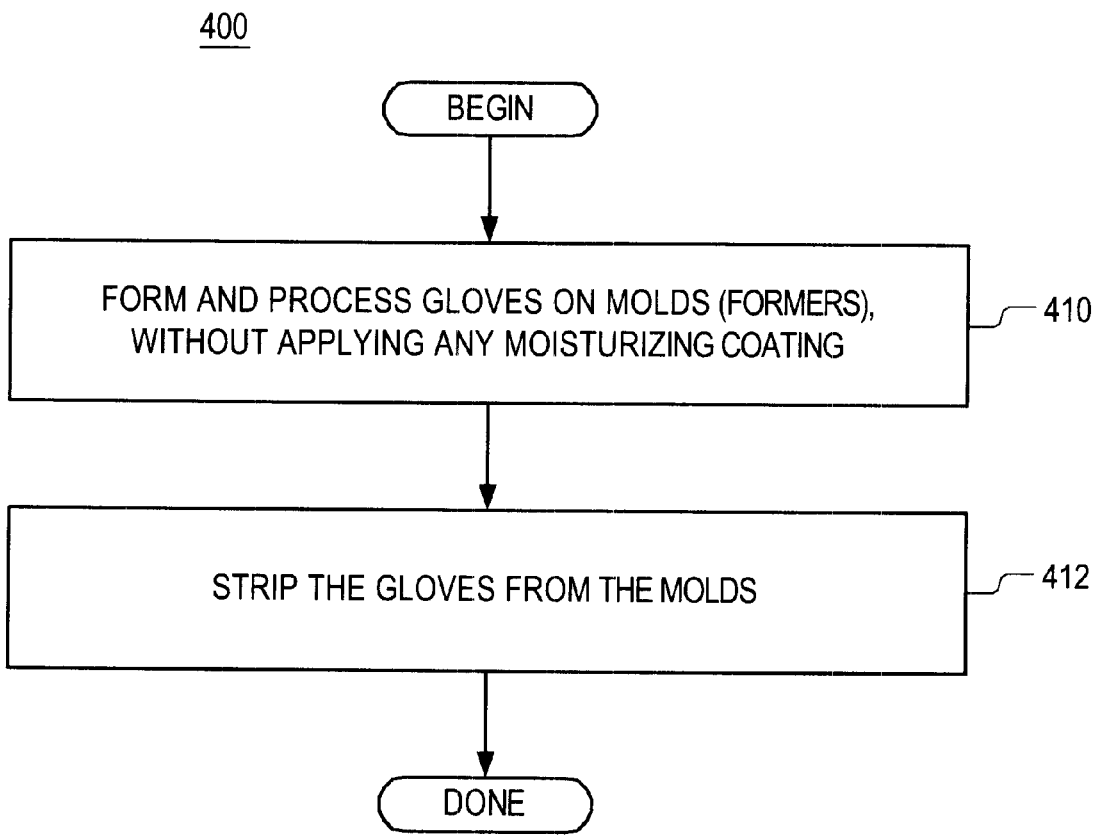
FIG. 4 is a flow diagram that illustrates a conventional method for manufacturing conventional examination gloves.

FIG. 4 is a flow diagram that illustrates a conventional method 400 for manufacturing conventional examination gloves. In a step 410, gloves are formed on molds by conventional processes. Each of these molds is shaped to be at least reminiscent of a hand such that the resulting gloves will fit hands. The forming and formed gloves undergo conventional processing on the molds in the step 410. Then, in a step 412, they are removed from the molds.

Figure 5:
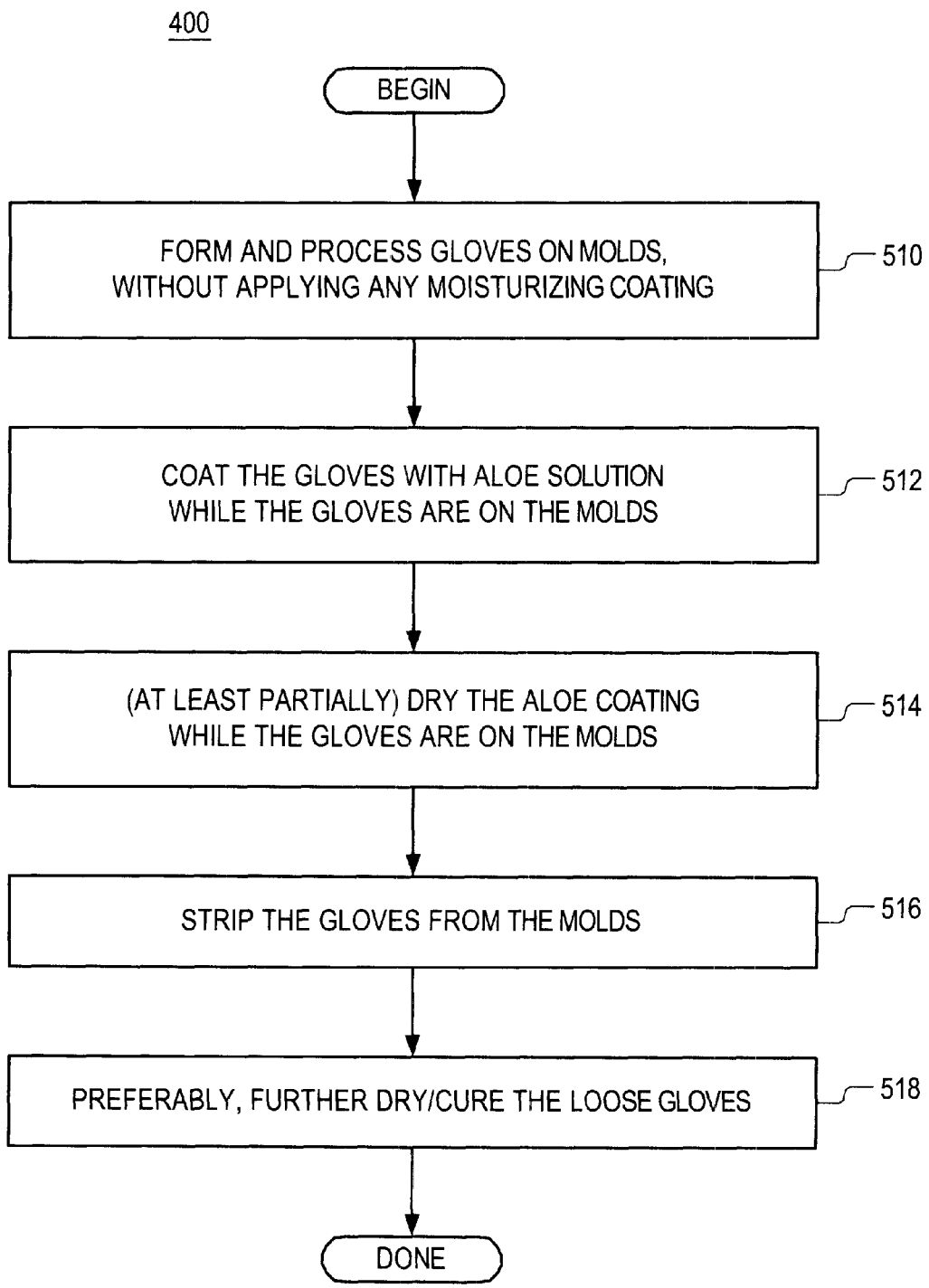
FIG. 5 is a flow diagram that illustrates a method, according to an embodiment of the present invention, for manufacturing Aloe Vera gloves that is integrated with, and includes, the manufacturing of the underlying Aloe Vera-free gloves themselves.

FIG. 5 is a flow diagram that illustrates a method 500, according to an embodiment of the present invention. The method 500 is a method for manufacturing Aloe Vera gloves that is integrated with, and includes, the manufacturing of the underlying Aloe Vera-free gloves themselves. Preferably, the method 500 is fully automated within a production line. In a step 510, gloves are formed on molds using any competent technique, for example, using conventional processes as discussed in connection with FIG. 4. The forming and formed gloves undergo processing on the molds in the step 510 using, for example, conventional processing. In a step 512, an Aloe Vera solution, for example, the solution discussed earlier, is applied to the gloves while the gloves are still on the form. The application of the solution can be via any competent technique, for example, spraying, immersing, pouring, overfilling, dipping, and the like, (which are not mutually exclusive techniques). In a step 514, the Aloe Vera solution that coats the gloves undergoes at least partial, and preferably full or at least substantial, dehydration. Next, in a step 516, the gloves are removed from the molds. Preferably, after removal from the molds, the gloves are further dried and cured by heat, in a step 518.

In the step 510, the gloves formed on the mold are preferably considered to be inside out such that the interior of each glove, as later to be worn on the hand, faces outward. The gloves are formed and processed using whatever technique is competent to produce a glove of the desired material. The preferred material is natural rubber latex. After a glove is formed, while on the mold, the later hand-facing surface of the glove is preferably made safer, and/or easier to slide during donning, for later contact with hands, either by cleaning off any residual proteins, chemicals, and the like, for example, using chlorine, or by coating the surface with a thin insulating layer that will attempt to insulate the hand from contact with the residual proteins, chemicals, and the like during wearing of the glove. By being cleaned, the glove is likely to be slicker and easier to slide over skin during donning, especially if the glove is made of natural rubber latex. Similarly, the insulating layer is preferably made of a substance that is more slippery than the underlying glove. For example, even if the glove is a vinyl glove of a type that is not made significantly safer or more slippery by cleaning, it may still be coated with an insulating layer to increase its slippery-ness and thereby be made easier to don. The insulating layer is, for example, a polymer layer, for example, of silicone or polyurethane, In the step 512, Aloe Vera solution, such as has already been described, is applied to the gloves while the gloves are still on the molds, either by dipping or by spraying. If spraying is used, it should be thorough enough so as to leave a desired amount of solution on the gloves' inside out surfaces, for example, an amount comparable to that which would be obtained from dipping.

In the step 514, the gloves undergo at least partial, and preferably full or at least substantial, dehydration. For example, fanned heated air may be blown across the gloves on the molds. For natural rubber latex gloves, especially, the air is preferably not more than about 80° C., and even more preferably, the air is not more than about 65° C. Preferably, the Aloe Vera coating is sufficiently dried to provide sufficient adhesion between the Aloe Vera coating and the glove so that the coated glove can withstand the next step 516.

In the step 516, the gloves are stripped from the molds.

In the optional step 518, the loose gloves are further cured, and their Aloe Vera coatings are even further dehydrated by heat, for example, in a dryer as has been discussed earlier.

The forming and processing of gloves on molds in the step 510, in one example, includes, on an automatic production line: cleaning porcelain formers (molds) using hot water (for example, about 40° C. to 100° C.); drying the porcelain formers in hot air (for example, at about 40° C. to 100° C.); dipping the formers in coagulant (for example, at about 40° C. to 70° C.); drying the coagulant on the formers in hot air (for example, at about 35° C. to 140° C.); dipping the coagulant-coated formers in latex (for example, at about 25° C. to 45° C.); curing the latex on the formers in hot air (for example, at about 60° C. to 140° C.); leaching the gloves on the formers; beading the edge of the gloves on the formers; and then making the glove surfaces safer, and easier to don, for later contact with hands, either by cleaning or by coating the surface, as discussed above. If cleaning is used in the making-safer/making-easier-to-don step, then the forming and processing further includes: further curing (for example, at about 80° C. to 140° C.); rinsing with cold water (for example, at no more than room temperature); chlorination (for example, at no more than about 30° C.); preferably preceded by further rinsing with cold water (for example, at no more than room temperature); neutralization; further rinsing (for example, with hot followed by cold water); and dehydration and further curing in hot air. Alternatively, if coating is used in the making-safer/making-easier-to-don step, then the forming and processing further includes: drying in hot air (for example, at about 80° C. to 150° C.); coating with polymer (for example, at no more than about 45° C.); and further drying and curing in hot air (for example, at about 80° C. to 150° C.).

In addition to the preferred natural rubber latex, the present invention may be embodied as Aloe Vera-coated gloves of acrylonitrile, polyvinyl chloride, polyurethane, chloroprene, neoprene, butadiene, or the like, and their manufacturer. Further, in addition to Aloe Vera, the present invention may be embodied to alternatively or additionally use any other skin-soothing or skin-moisturizing substance or mixture that can be dried onto the inside of a glove and that, in the dry form, is mixed with moisture that consists only of perspiration from a hand during wearing of the glove and moisturizes the hand.

While the invention is described in some detail with specific reference to a few preferred embodiments and some alternatives, there is no intent to limit the invention to the particular embodiments or the specific alternatives. Thus, the true scope of the present invention is not limited to any one of the foregoing exemplary embodiments.

What is claimed is:

1. A method of manufacturing protective gloves, the method comprising:

forming a glove on a mold;

applying a solution that includes Aloe Vera onto at least a portion of the glove while the glove is on the mold;

at least partially drying the solution that has been applied onto the glove while the glove is on the mold; and removing the glove from the mold;

wherein, when the glove is worn on a hand, the portion of the glove having the aloe vera is to face the skin of the hand.

2. The method of claim 1, wherein the steps of forming, applying, at least partially drying, and removing are performed on an automatic production line.

3. The method of claim 1, wherein the step of at least partially drying includes at least substantially drying the solution that has been applied onto the glove while the glove is on the mold.

4. The method of claim 1, further including a step of further drying the solution that has been applied onto the glove after the glove is no longer on the mold.

5. The method of claim 4, wherein the step of further drying the solution comprises tumbling a plurality of loose gloves in a heat dryer.

6. The method of claim 1, wherein the step of applying the solution comprises spraying the solution onto the glove while the glove is on the mold.

7. The method of claim 6, wherein the glove on the mold is considered to be inside out, whereby an outward-facing surface of the glove that is on the mold is the surface that will face a hand when the glove is worn.

8. The method of claim 1, wherein the step of applying the solution comprises dipping the glove while the glove is on the mold into a quantity of the solution.

9. The method of claim 1, wherein the step of at least partially drying comprises blowing heated air onto the glove while the glove is on the mold.

10. The method of claim 1, wherein the solution includes substantially only water and Aloe Vera.

11. The method of claim 1, further including a step of further drying the solution that has been applied onto the glove after the glove is no longer on the mold, wherein:

the method is performed on an automatic production line;

the glove on the mold is considered to be inside out, whereby an outward-facing surface of the glove that is on the mold is the surface that will face a hand when the glove is worn;

the solution includes substantially only water and Aloe Vera;

the step of applying the solution comprises spraying the solution onto the glove while the glove is on the mold the step of at least partially drying includes blowing heated air onto the glove while the glove is on the mold to at least substantially dry the solution that has been applied onto the glove; and the step of further drying the solution comprises tumbling a plurality of loose gloves in a heat dryer.

12. A protective glove that is manufactured according to the method of claim 11.

13. A protective glove that is manufactured according to claim the method of 1.

14. The protective glove of claim 13, wherein the glove is made of natural rubber latex.

15. The method of claim 1, wherein the step of forming the glove on the mold comprises coating the glove with an insulating layer that will at least to some degree insulate the hand from the glove during wearing.

16. The method of claim 15, wherein the insulating layer includes a polymer layer.

17. The method of claim 1, wherein the step of forming the glove on the mold comprises cleaning a surface of the glove to remove contaminants to thereby make safer later contact between the surface and a hand that will wear the glove.

* * * * *